(12) United States Patent
Haller et al.

(10) Patent No.: US 7,729,758 B2
(45) Date of Patent: Jun. 1, 2010

(54) MAGNETICALLY COUPLED MICROSTIMULATORS

(75) Inventors: Matthew I. Haller, Valley Village, CA (US); Jordi Parramon, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 1081 days.

(21) Appl. No.: 11/291,464

(22) Filed: Nov. 30, 2005

(65) Prior Publication Data

US 2007/0123938 A1 May 31, 2007

(51) Int. Cl.
*A61N 1/36* (2006.01)

(52) U.S. Cl. .................. 607/2; 600/13; 607/3; 607/36; 607/60; 607/61; 607/116

(58) Field of Classification Search .............. 600/13, 600/14; 607/2, 3, 36, 61, 32, 33, 60, 65, 607/118, 116; 128/903
See application file for complete search history.

(56) References Cited

U.S. PATENT DOCUMENTS

| | | |
|---|---|---|
| 3,760,984 A | 9/1973 | Theeuwes |
| 3,845,770 A | 11/1974 | Theeuwes et al. |
| 3,850,161 A | 11/1974 | Liss |
| 3,881,495 A | 5/1975 | Pannozzo |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,203,440 A | 5/1980 | Theeuwes |
| 4,203,442 A | 5/1980 | Michaels |
| 4,210,139 A | 7/1980 | Higuchi |
| 4,232,679 A | 11/1980 | Schulman |
| 4,327,725 A | 5/1982 | Cortese et al. |
| 4,360,019 A | 11/1982 | Portner et al. |
| 4,408,608 A | 10/1983 | Daly et al. |
| 4,424,812 A | 1/1984 | Lesnick |
| 4,481,950 A | 11/1984 | Duggan |
| 4,487,603 A | 12/1984 | Harris |
| 4,556,061 A | 12/1985 | Barreras et al. |
| 4,562,751 A | 1/1986 | Nason et al. |
| 4,590,946 A | 5/1986 | Loeb |
| 4,608,985 A | 9/1986 | Crish et al. |
| 4,612,934 A | 9/1986 | Borkan |
| 4,627,850 A | 12/1986 | Deters et al. |
| 4,628,942 A | 12/1986 | Sweeney et al. |
| 4,649,936 A | 3/1987 | Ungar et al. |
| 4,678,408 A | 7/1987 | Nason et al. |
| 4,685,903 A | 8/1987 | Cable et al. |
| 4,690,144 A | 9/1987 | Rise et al. |

(Continued)

FOREIGN PATENT DOCUMENTS

WO  01/82398  11/2001

(Continued)

*Primary Examiner*—Carl H Layno
*Assistant Examiner*—Jennifer Stewart
(74) *Attorney, Agent, or Firm*—Vista IP Law Group LLP (57) ABSTRACT

Disclosed are implantable electronic devices and systems including a pair of microstimulators. The microstimulators include coils that are energized to generate magnetic fields aligned along a common axis.

25 Claims, 9 Drawing Sheets

U.S. PATENT DOCUMENTS

| | | |
|---|---|---|
| 4,692,147 A | 9/1987 | Duggan |
| 4,702,254 A | 10/1987 | Zabara |
| 4,725,852 A | 2/1988 | Gamblin et al. |
| 4,793,353 A | 12/1988 | Borkan |
| 4,865,845 A | 9/1989 | Eckenhoff et al. |
| 5,057,318 A | 10/1991 | Magruder et al. |
| 5,059,423 A | 10/1991 | Magruder et al. |
| 5,080,653 A | 1/1992 | Voss et al. |
| 5,095,904 A | 3/1992 | Seligman et al. |
| 5,097,122 A | 3/1992 | Colman et al. |
| 5,112,614 A | 5/1992 | Magruder et al. |
| 5,137,727 A | 8/1992 | Eckenhoff |
| 5,188,104 A | 2/1993 | Wernicke et al. |
| 5,193,539 A | 3/1993 | Schulman et al. |
| 5,193,540 A | 3/1993 | Schulman et al. |
| 5,199,430 A | 4/1993 | Fang et al. |
| 5,215,086 A | 6/1993 | Terry et al. |
| 5,234,692 A | 8/1993 | Magruder et al. |
| 5,234,693 A | 8/1993 | Magruder et al. |
| 5,299,569 A | 4/1994 | Wernicke et al. |
| 5,305,445 A | 4/1994 | Nishikawa |
| 5,305,745 A | 4/1994 | Zacouto |
| 5,312,439 A | 5/1994 | Loeb |
| 5,314,451 A | 5/1994 | Mulier |
| 5,314,458 A | 5/1994 | Najafi et al. |
| 5,324,316 A | 6/1994 | Schulman et al. |
| 5,330,515 A | 7/1994 | Rutecki et al. |
| 5,358,514 A | 10/1994 | Schulman et al. |
| 5,405,363 A | 4/1995 | Kroll et al. |
| 5,405,367 A | 4/1995 | Schulman et al. |
| 5,501,703 A | 3/1996 | Holsheimer et al. |
| 5,531,787 A | 7/1996 | Lesinski et al. |
| 5,571,148 A * | 11/1996 | Loeb et al. .................... 607/57 |
| 5,591,217 A | 1/1997 | Barreras |
| 5,697,951 A * | 12/1997 | Harpstead et al. .............. 607/3 |
| 5,700,282 A | 12/1997 | Zabara |
| 5,716,318 A | 2/1998 | Manning |
| 5,728,396 A | 3/1998 | Peery et al. |
| 5,752,979 A | 5/1998 | Benabid |
| 5,755,750 A | 5/1998 | Petruska et al. |
| 5,782,891 A | 7/1998 | Hassler et al. |
| 5,895,416 A | 4/1999 | Barreras et al. |
| 5,938,584 A | 8/1999 | Ardito et al. |
| 5,938,688 A | 8/1999 | Schiff |
| 5,995,868 A | 11/1999 | Dorfmeister et al. |
| 6,010,316 A | 1/2000 | Haller et al. |
| 6,016,449 A | 1/2000 | Fischell et al. |
| 6,051,017 A | 4/2000 | Loeb et al. |
| 6,104,956 A | 8/2000 | Naritoku et al. |
| 6,112,116 A | 8/2000 | Fischell et al. |
| 6,154,678 A | 11/2000 | Lauro |
| 6,164,284 A | 12/2000 | Schulman et al. |
| 6,178,349 B1 | 1/2001 | Kieval |
| 6,185,452 B1 | 2/2001 | Schulman et al. |
| 6,205,359 B1 | 3/2001 | Boveja |
| 6,208,894 B1 | 3/2001 | Schulman et al. |
| 6,214,032 B1 | 4/2001 | Loeb et al. |
| 6,216,045 B1 | 4/2001 | Black et al. |
| 6,219,580 B1 | 4/2001 | Faltys et al. |
| 6,266,564 B1 | 7/2001 | Hill et al. |
| 6,272,382 B1 | 8/2001 | Faltys et al. |
| 6,275,737 B1 | 8/2001 | Mann |
| 6,280,873 B1 | 8/2001 | Tsukamoto |
| 6,308,101 B1 | 10/2001 | Faltys et al. |
| 6,341,236 B1 | 1/2002 | Osorio et al. |
| 6,368,315 B1 | 4/2002 | Gillis et al. |
| 6,381,496 B1 | 4/2002 | Meadows et al. |
| 6,424,234 B1 | 7/2002 | Stevenson |
| 6,458,171 B1 | 10/2002 | Tsukamoto |
| 6,473,652 B1 | 10/2002 | Sarwal et al. |
| 6,487,446 B1 | 11/2002 | Hill et al. |
| 6,516,227 B1 | 2/2003 | Meadows et al. |
| 6,526,318 B1 | 2/2003 | Ansarinia |
| 6,539,263 B1 | 3/2003 | Schiff et al. |
| 6,553,263 B1 | 4/2003 | Meadows et al. |
| 6,560,490 B2 | 5/2003 | Grill et al. |
| 6,582,441 B1 | 6/2003 | He et al. |
| 6,597,954 B1 | 7/2003 | Pless et al. |
| 6,600,954 B2 | 7/2003 | Cohen et al. |
| 6,620,151 B2 | 9/2003 | Blischak et al. |
| 6,622,048 B1 | 9/2003 | Mann et al. |
| 6,631,296 B1 | 10/2003 | Parramon et al. |
| 6,650,943 B1 | 11/2003 | Whitehurst et al. |
| 6,662,035 B2 | 12/2003 | Sochor |
| 6,665,562 B2 | 12/2003 | Gluckman |
| 6,666,845 B2 | 12/2003 | Hooper et al. |
| 6,712,753 B2 | 3/2004 | Manne |
| 6,733,485 B1 | 5/2004 | Whitehurst et al. |
| 6,740,072 B2 | 5/2004 | Starkweather et al. |
| 6,760,626 B1 | 7/2004 | Boveja |
| 6,770,067 B2 | 8/2004 | Lorenzen et al. |
| 6,782,292 B2 | 8/2004 | Whitehurst |
| 6,826,428 B1 | 11/2004 | Chen et al. |
| 6,856,838 B2 | 2/2005 | Parramon et al. |
| 6,907,295 B2 | 6/2005 | Gross et al. |
| 6,928,320 B2 | 8/2005 | King |
| 7,072,720 B2 | 7/2006 | Puskas |
| 7,186,209 B2 * | 3/2007 | Jacobson et al. .............. 600/13 |
| 7,200,504 B1 | 4/2007 | Fister |
| 7,203,548 B2 | 4/2007 | Whitehurst et al. |
| 7,292,890 B2 | 11/2007 | Whitehurst et al. |
| 2001/0003799 A1 | 6/2001 | Boveja |
| 2001/0046625 A1 | 11/2001 | Ruth et al. |
| 2001/0053476 A1 | 12/2001 | Ruth et al. |
| 2002/0016615 A1 | 2/2002 | Dev et al. |
| 2002/0022873 A1 | 2/2002 | Erickson et al. |
| 2003/0004546 A1 | 1/2003 | Casey |
| 2003/0203890 A1 | 10/2003 | Steiner et al. |
| 2003/0236557 A1 | 12/2003 | Whitehurst et al. |
| 2003/0236558 A1 | 12/2003 | Whitehurst et al. |
| 2004/0015204 A1 | 1/2004 | Whitehurst et al. |
| 2004/0015205 A1 | 1/2004 | Whitehurst et al. |
| 2004/0034394 A1 | 2/2004 | Woods et al. |
| 2004/0059392 A1 | 3/2004 | Parramon et al. |
| 2004/0068298 A1 | 4/2004 | Parramon et al. |
| 2004/0082908 A1 | 4/2004 | Whitehurst et al. |
| 2004/0088032 A1 | 5/2004 | Haller et al. |
| 2004/0172089 A1 | 9/2004 | Whitehurst et al. |
| 2004/0243182 A1 | 12/2004 | Cohen et al. |
| 2005/0004619 A1 | 1/2005 | Wahlstrand et al. |
| 2005/0021108 A1 | 1/2005 | Klosterman et al. |
| 2005/0057905 A1 | 3/2005 | He et al. |
| 2005/0101878 A1 | 5/2005 | Daly et al. |
| 2005/0131494 A1 | 6/2005 | Park et al. |
| 2005/0131495 A1 | 6/2005 | Parramon et al. |
| 2005/0131496 A1 | 6/2005 | Parramon et al. |
| 2005/0143781 A1 | 6/2005 | Carbunaru et al. |
| 2005/0245971 A1 | 11/2005 | Brockway et al. |
| 2005/0267546 A1 | 12/2005 | Parramon et al. |
| 2006/0184204 A1 | 8/2006 | He |
| 2006/0195143 A1 | 8/2006 | McClure et al. |
| 2006/0212087 A1 | 9/2006 | Haller et al. |
| 2006/0229688 A1 | 10/2006 | McClure et al. |
| 2007/0021800 A1 | 1/2007 | Whitehurst et al. |
| 2007/0112404 A1 | 5/2007 | Mann et al. |

FOREIGN PATENT DOCUMENTS

| | | |
|---|---|---|
| WO | 03/005465 | 1/2003 |
| WO | 04/000416 | 12/2003 |
| WO | 04/002572 | 1/2004 |
| WO | WO 2007/059343 | 5/2007 |

* cited by examiner

MAGNETICALLY COUPLED MICROSTIMULATORS

BACKGROUND

The present disclosure relates to implantable electronic devices and systems.

Implantable electronic devices and systems, such as neurostimulators, create an electrical stimulus that is transferred to the nerves and tissues of a patient's body in order to treat a variety of biological disorders. For example, pacemakers can be used to treat cardiac arrhythmia, defibrillators can be used to treat cardiac fibrillation, cochlear stimulators can be used to treat deafness, retinal stimulators can be used to treat blindness, muscle stimulators can be used to treat paralysis in limbs, spinal cord stimulators can be used to treat chronic pain, cortical and deep brain stimulators can be used to treat motor and psychological disorders, and other neural stimulators can be used to treat disorders such as urinary urge incontinence, sleep apnea, and sexual dysfunction.

As there are a number of different applications, there are similarly varying types of implantable electronic devices and systems. For example, a spinal cord stimulator can be used to treat chronic pain, while a microstimulator can be used to treat disorders such as urinary urge incontinence, sleep apnea, or sexual dysfunction. As such, the features of the implantable electronic device, such as, for example, the size, shape, orientation, and functional components of the device, can vary with the nature of the application for which it is used. It is generally desirably that the aforementioned features are configured to render the device as compact as possible so as to consume a small amount of space when implanted in the body.

SUMMARY

Disclosed is a microstimulation system that includes a pair of microstimulators wherein one of the microstimulators can be positioned inside a cavity in another microstimulator. The microstimulators include coils that are energized to generate magnetic fields that are co-axially aligned on an axis. The alignment of the magnetic fields forms a generally strong inductive coupling between the coils of the microstimulators. Because one microstimulator is positioned inside of the other microstimulator and the two are aligned along a common axis L, the two devices collectively use up less space than if placed side by side.

In one aspect, there is disclosed a system of magnetically coupled stimulators. The system includes a first stimulator for implanting in a body of a patient and a second stimulator for implanting in a body of a patient. The first stimulator has a first coil and the second stimulator has a second coil. The first and second coils generate a magnetic field aligned along a common axis.

In another aspect, there is disclosed a stimulator for implanting in a patient. The stimulator includes a housing having an internal cavity sized to receive a second stimulator. The stimulator further includes a first coil that generates a magnetic field, wherein the magnetic field is aligned along a common axis with a magnetic field generated by a second coil of a second stimulator when the second stimulator is positioned in the cavity.

In another aspect, there is disclosed a method, comprising implanting a first stimulator in the body of a patient, the first stimulator having a first coil; implanting a second stimulator in the body of the patient, the second stimulator having a second coil; and energizing the first and second coils such that the first and second coils generate magnetic fields that are aligned along a common axis.

The details of one or more implementations are set forth in the accompanying drawings and the description below. Further features, aspects, and advantages will become apparent from the description, the drawings, and the claims.

BRIEF DESCRIPTION OF THE DRAWINGS

Like reference symbols indicate like elements throughout the specification and drawings.

DETAILED DESCRIPTION

An implementation can utilize one or more implantable electronic devices, including microstimulators. It will be recognized that the term microstimulator may include an implantable pulse generator (IPG) coupled to a lead of electrodes, a spinal cord stimulator (SCS), a cochlear implant, a deep brain stimulator, a drug pump, a microstimulator, a micro-drug pump or any other type of implantable stimulator configured to deliver electrical and/or drug stimulation.

Exemplary IPGs suitable for use as described herein include, but are not necessarily limited to, those disclosed in U.S. Pat. Nos. 6,381,496, 6,553,263; and 6,760,626.

Exemplary spinal cord stimulators suitable for use as described herein include, but are not necessarily limited to, those disclosed in U.S. Pat. Nos. 5,501,703; 6,487,446; and 6,516,227.

Exemplary cochlear implants suitable for use as described herein include, but are not necessarily limited to, those disclosed in U.S. Pat. Nos. 6,219,580; 6,272,382; and 6,308,101.

Exemplary deep brain stimulators suitable for use as described herein include, but are not necessarily limited to, those disclosed in U.S. Pat. Nos. 5,938,688; 6,016,449; and 6,539,263.

Exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Additional drug pumps may include convective drug delivery system, e.g., systems based upon electroosmosis, vapor pressure pumps, electrolytic pumps, effervescent pumps, piezoelectric pumps and osmotic pumps. Such pumps or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like.

Exemplary microstimulators suitable for use as described herein include, but are not necessarily limited to, those disclosed in U.S. Pat. Nos. 5,193,539; 5,193,540; 5,312,439; 6,185,452; 6,164,284; 6,208,894; and 6,051,017.

Exemplary micro-drug pumps suitable for use as described herein include, but are not necessarily limited to, those disclosed in U.S. Patent Pub. No. 2004/0082908 and U.S. Pat. Nos. 5,234,692; 5,234,693; 5,728,396; 6,368,315; 6,666,845; and 6,620,151. All of the aforementioned patents and publications are incorporated herein by reference in their respective entireties.

Figure 1:
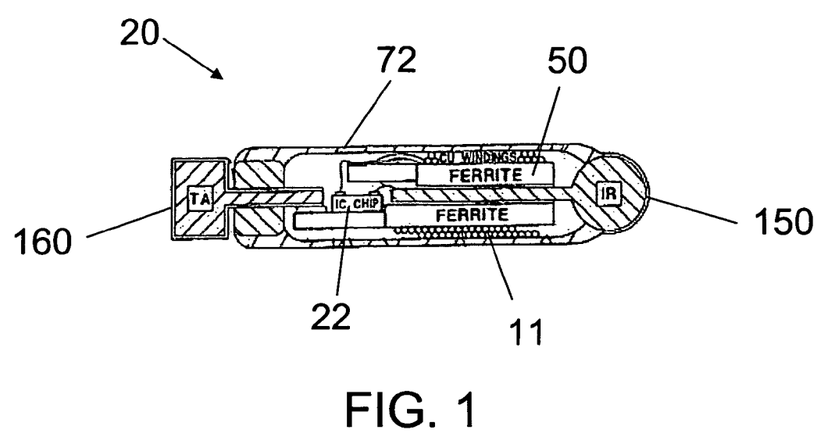
FIG. 1 is a block diagram of an implantable electronic microstimulator device.

FIG. 1 shows an exemplary implementation of an implantable electronic microstimulator 20 that is configured to be implanted into a patient. When implanted, the microstimulator 20 provides stimulation to surrounding nerves and tissues. The microstimulator 20 includes a housing 72 that is hermetically sealed at opposed ends and that contains electronic circuitry disposed inside of the housing 72. In an exemplary embodiment, the electronic circuitry of the microstimulator 20 includes an integrated circuit (IC) chip 22, a ferrite core 50, and a coil 11 wound around the ferrite core 50. The IC chip 22 can include several logic and other circuits, including programmable memory and a power source.

The electrical circuitry is connected to electrodes 150 and 160, which can deliver electrical stimulation to surrounding tissues and nerves when the microstimulator 20 is implanted in a patient. The electrodes 150 and 160 can comprise leadless electrodes that pass through the housing 72. Alternatively, the electrodes 150 and 160 can be affixed to leads and thus be positioned away from the housing 72 by a distance suitable for the intended application. The electrodes 150 and 160 generally comprise a stimulating electrode, which is placed in proximity to the nerve or tissue that is to be stimulated, and an indifferent electrode, which completes the circuit and thereby facilitates electrical stimulation.

All of the components and circuits within the microstimulator 20 are interconnected in circuit relationship so as to function in a predetermined manner. In one embodiment, the components and circuits function as follows: (a) the coil 11 is inductively coupled to a modulated power signal that is generated external to the housing 72 (as described below); (b) the inductive coupling induces a modulated power signal in the coil 11; (c) the induced modulated power signal is rectified to provide operating power for the IC chip 22; (d) power from the rectified power signal charges a storage capacitor (which may be internal to the microstimulator 20, or formed by its electrodes); (e) the power signal is demodulated to extract an address word therefrom; (f) the extracted address word is compared to a preprogrammed microstimulator code stored in the microstimulator; and (g) if the extracted address code matches the preprogrammed microstimulator code, as determined by logic circuits included within the IC chip 22, the capacitor is discharged through the two electrodes 150 and 160 with an amplitude and pulse width determined by the incoming data stream. In this manner, the operation of the microstimulator, i.e., the selective discharging of its storage capacitor, is controlled through appropriate modulation of the power signal.

The external surfaces of the housing 72 can be constructed of one or more biocompatible materials, including glass, ceramic, or other material that provides a hermetic package capable of excluding water vapor and permitting the passage of electromagnetic fields, such as the electromagnetic fields used to transfer power and/or signals to the microstimulator 20. In another implementation, the external surfaces of the housing 72 can be constructed of a noble metal or compound, or some combination of a noble metal or compound and one or more biocompatible materials, such as glass or ceramic.

The electrodes 150 and 160 may be made of a conducting ceramic, conducting polymer, and/or a noble or refractory metal, such as gold, silver, platinum, iridium, tantalum, titanium, titanium nitride, niobium or their alloys that, e.g., minimize corrosion, electrolysis, and damage to the surrounding tissues and/or the device The programmable memory included in the microstimulator 20 can be used to store data, such as stimulation parameters and control parameters. The data stored in the programmable memory can be communicated to, or reprogrammed by, an external device through one-way or bi-directional communication. Additionally, the electrical circuitry can be configured to store data in the programmable memory during operation of the microstimulator 20.

The electrical circuitry included in the microstimulator 20 can include circuitry for receiving power and/or signals transmitted by an external source by inductive, radio frequency (RF), or other electromagnetic coupling. In an implementation, the inductive coil 11 is configured for receiving power from an electromagnetic field, and for receiving and/or transmitting data via one or more electromagnetic fields. Further, the integrated circuits of chip 22 are configured for performing control functions, such as decoding and storing data received from an external source, generating stimulation pulses based on stimulation parameters, and monitoring the state of charge of the power source. Additionally, the electrical circuitry can further include discrete electronic components used to perform the functions of the microstimulator 20, such as capacitors, resistors, transistors, and demodulators.

The power source can be an electrolytic capacitor or a secondary battery, such as a lithium-ion or a lithium-ion polymer battery. Other possible power options include but are not limited to a primary battery, a rechargeable and/or replenishable battery (e.g., a lithium ion battery that is recharged or replenished via an external and/or internal power source), a super capacitor, an ultra capacitor, a nuclear battery, a mechanical resonator, an external or alternate internal power source coupled to the stimulator (e.g., via an RF, infrared, optical, thermal, or other energy-coupling link through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell (much like a battery, but does not run down or require recharging, but requires only a fuel), a bioelectrical cell (where two or more electrodes use tissue-generated potentials and currents to capture energy and convert it to useable power), an osmotic pressure pump (where mechanical energy is generated due to fluid ingress), or the like.

In order to monitor, control, and protect the power source, the electrical circuitry also can include circuitry for recharging the power source, such as the charging control circuit described below.

In another implementation, the implantable electronic device can comprise a different type of device that is adapted to the requirements of a different application. For example, the implantable electronic device can comprise a spinal cord stimulator device that is adapted to treat chronic pain. Alternatively, the implantable electronic device can comprise a pacemaker adapted to treat cardiac arrhythmia. Regardless of the intended application, the implantable electronic device implementation can include a type of power source and various electrical circuitry for monitoring, controlling, and protecting the power source.

Figure 2:
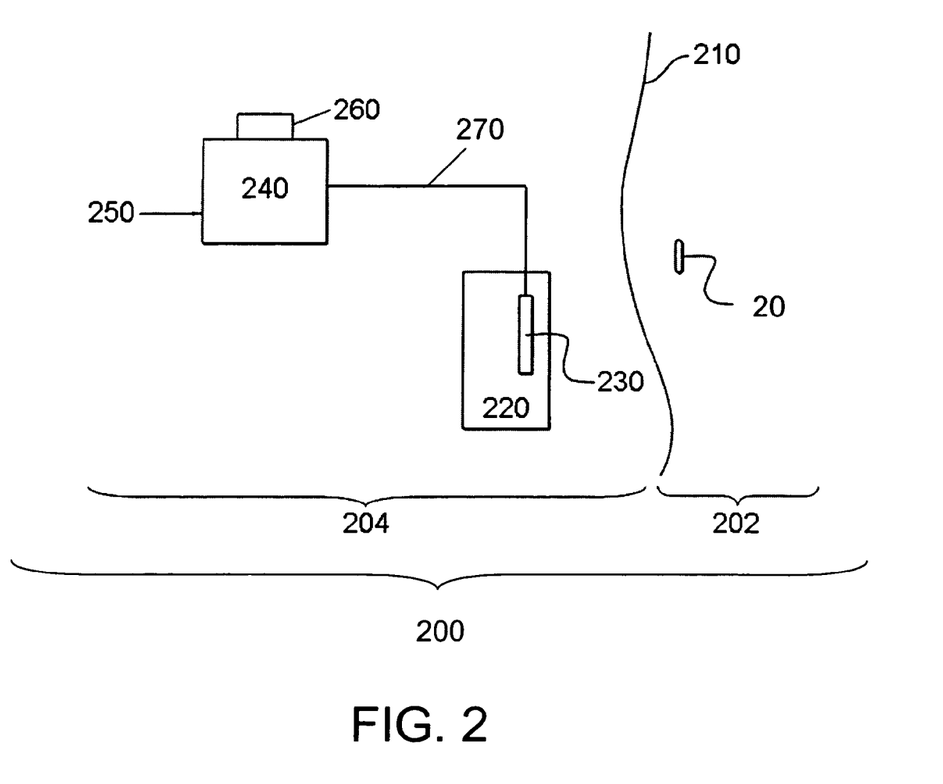
FIGS. 2-3 are functional block diagrams of a stimulation system.

As shown in FIG. 2, the microstimulator 20 can comprise a portion of a stimulator system 200 that includes an internal portion 202 and an external portion 204. In the system of FIG. 2, the internal portion 202 lies inside of the body of a patient 210 and is comprised of one or more microstimulators, including the microstimulator 20. The external portion 204 of the stimulator system 200 comprises a control system that is used to communicate with, and provide power to, the one or more microstimulators 20 included in the internal portion 202.

In an implementation, the patient 210 is positioned within the operating range an external interface 220 when a device charging operation or communication with the microstimulator 20 is to be initiated. The external interface 220 can include one or more inductive coils 230 that are used to generate an electromagnetic field. The electromagnetic field can be generated with sufficient strength to penetrate the tissue of the patient 210 beyond the minimum implant depth of the microstimulator 20. The microstimulator 20 can thereby be inductively coupled with the external interface 220 and thus the external controller 240. As described below, the microstimulator can also be inductively coupled to one or more other microstimulators 20.

The external controller 240 provides signals and power to the external interface 220 through a cable interface 270. The external interface 220 can also provide signals to the external controller 240 through the cable interface 270. In another implementation, the external interface 220 and the external controller 240 can communicate through a wireless interface (not shown) instead of, or in addition to, the cable interface 270. In such an implementation, the external interface 220 further can include an independent power supply, such as a connection to a conventional power source or a battery.

The external controller 240 also can include a connection to a conventional power source 250, such as an alternating current adapter. Additionally, the external controller 240 can include a control interface 260 that receives input from one or more users, such as a caregiver or a patient. The control interface 260 also can output information relating to the status and the configuration of the microstimulator 20 to the one or more users. The control interface 260 can be any control interface or combination of control interfaces known in the art, including a mouse, a keyboard, a keypad, a touch screen, a touch pad, a voice command interface, an electro-mechanical switch, a speaker, and a visual display device.

The external interface 220 can be embedded in a fixed location, such as a charging table, a charging chair, or a similar structure. In another implementation, the external interface 220 can be included in a portable object, such as a charging paddle, a cushion, a pillow, or a similar object. In such an implementation, the external interface 220 can be adapted to be worn by or affixed to the patient 210. For example, the external interface 220 can be worn on a belt, inserted into a pouch in a garment, or affixed to the patient using VELCRO® or an adhesive.

Figure 3:
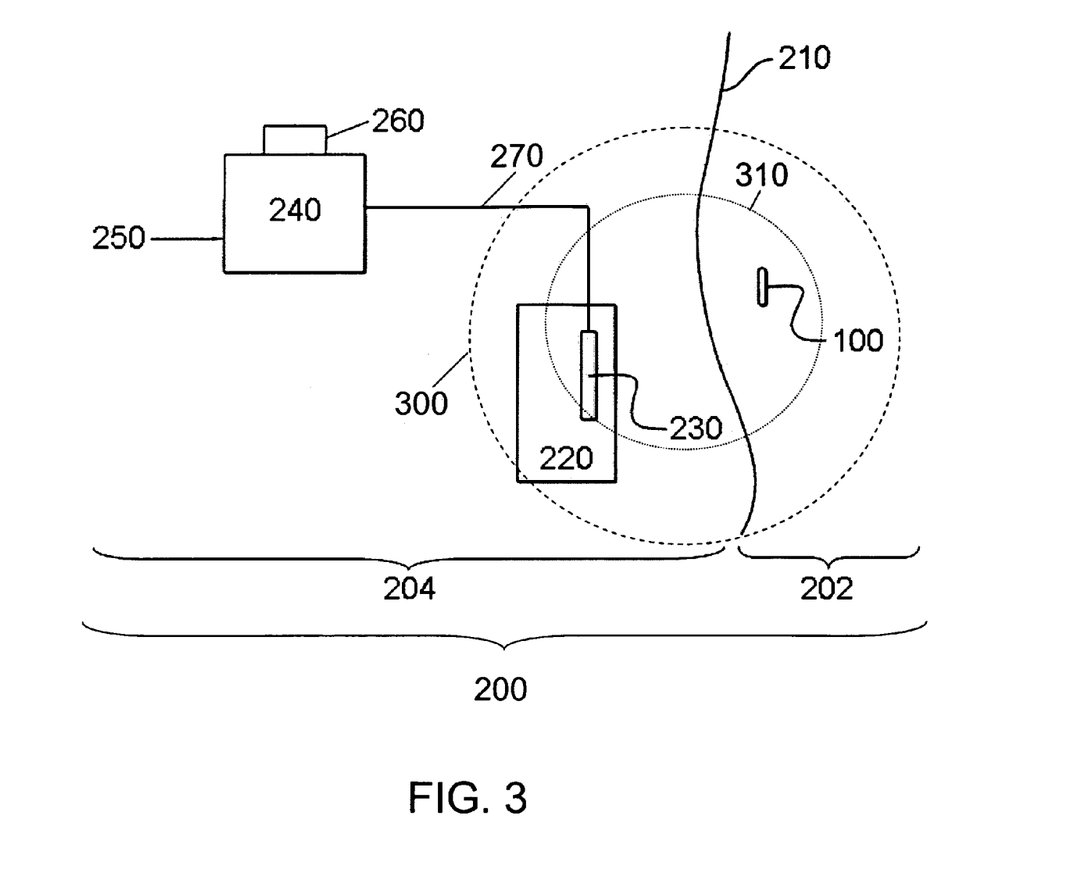

As shown in FIG. 3, the external interface 220 can be inductively coupled to the microstimulator 20 through an electromagnetic field 300 generated at the external interface 220. As a result of this inductive coupling, power and signals can be transmitted from the external interface 220 to the microstimulator 20. Similarly, the microstimulator 20 can be inductively coupled to the external interface 220, and thus to the external controller 240, through an electromagnetic field 310 generated by the microstimulator 20. The microstimulator 20 can thereby transmit signals to the external interface 220 and the external controller 240. In another implementation, signals can be transmitted between the external interface 220 and the microstimulator 20 using a single electromagnetic field.

Because the electromagnetic field 300 generated at the external interface 220 can interfere with or obscure the electromagnetic field 310 generated by the microstimulator 20, the stimulator system 200 can be configured such that only one electromagnetic field is generated at a given time. For example, generation of the electromagnetic field 300 at the external interface 220 can be stopped when the microstimulator 20 is expected to transmit. In another implementation, the microstimulator 20 can be configured to generate an electromagnetic field 310 only when the microstimulator 20 does not detect the presence of another electromagnetic field.

For certain situations, two or more of the implantable electronic devices are coupled to one another such that various methods and systems for magnetically coupling implantable electronic devices are needed. For example a pair of coils in the two devices can be inductively coupled to one another by positioning the devices in a generally juxtaposed relationship. When juxtaposed, the devices can consume an undesirably large amount of space. Thus, it is generally desirable that the devices be as small as possible so that they consume a small amount of space when implanted in the body.

Figure 4:
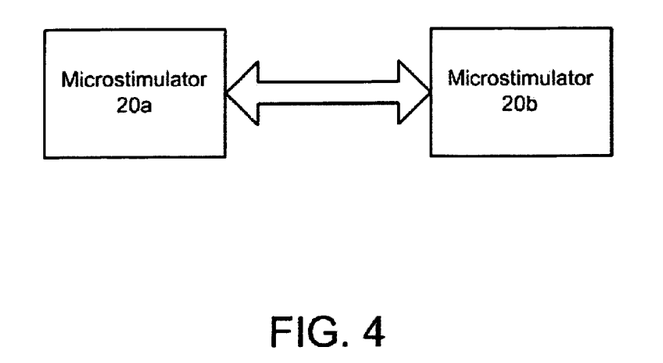
FIG. 4 is a schematic diagram of a pair of linked microstimulators.

FIG. 4 shows a first microstimulator 20a and a second microstimulator 20b inductively coupled to one another. (The microstimulators are referred to individually by reference numeral 20a or 20b and collectively by reference numeral 20.) The coupling occurs through an electromagnetic field generated by at least one of the microstimulators 20. In this manner, the first microstimulator 20a can transmit signals to the second microstimulator 20b.

The inductive coupling is accomplished by positioning the coil 11a (FIG. 6) of the first microstimulator 20a adjacent the coil 11b (FIG. 6) of the second microstimulator 20b. Depending on the geometric configuration of the first and second microstimulators 20a, 20b, the pair of microstimulators can consume a relatively large amount of space within the anatomy of the patient.

Figure 5A:
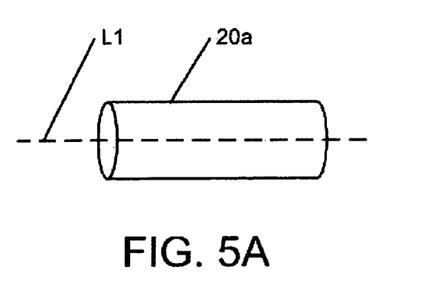
FIGS. 5A and 5B show first and second microstimulators that can be linked together both structurally and inductively.

There is now described a structural arrangement for first and second microstimulators that is configured to consume a relatively small amount of space and that is also configured to provide a strong inductive coupling between the microstimulators. FIG. 5A shows the first microstimulator 20a, which has a predetermined shape, such as a generally cylindrical shape. It should be appreciated that the microstimulator 20a can have other shapes, such as rectangle, square, oval, etc. Although not shown in FIG. 5A, the first microstimulator 20a includes some or all of the components of the microstimulator shown in FIG. 1. In particular, the microstimulator 20a includes an annular coil 11a (FIG. 6) that is generally annularly positioned around a longitudinal axis L1 of the microstimulator 20a.

Figure 5B:
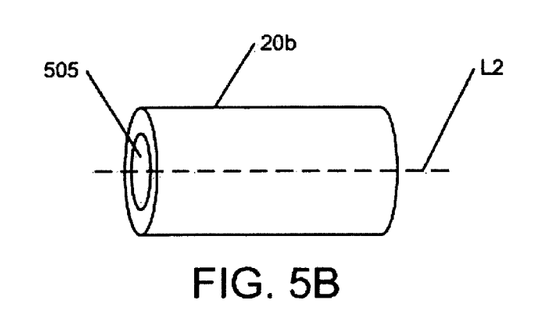

FIG. 5B shows the second microstimulator 20b, which has a predetermined shape, such as a generally cylindrical shape. It should be appreciated that the microstimulator 20b can have other shapes, such as rectangle, square, oval, etc. The second microstimulator 20b includes an internal cavity 505 that extends along a longitudinal axis L2 of the second microstimulator 20b. The internal cavity 505 has a size and shape that conforms to the size and shape of the first microstimulator 20a. That is, the cavity 505 is sized and shaped to receive the first microstimulator therein, such as in a sliding fashion. The cavity 505 can extend entirely through the microstimulator 20b such that openings are formed on both ends of the microstimulator 20b. Alternately, the cavity 505 can extend only partially through the microstimulator 20b such that only one end has an opening. In either case, the cavity 505 is sized and shaped to receive at least a portion of the first microstimulator 20a.

The second microstimulator 20b includes some or all of the components of the microstimulator shown in FIG. 1, including an annular coil 11b (FIG. 6) that is disposed around the longitudinal axis L2. Thus, the annular coil of the second microstimulator 20b is positioned in an annular fashion around the circumference or perimeter of the cavity 505.

Figure 6:
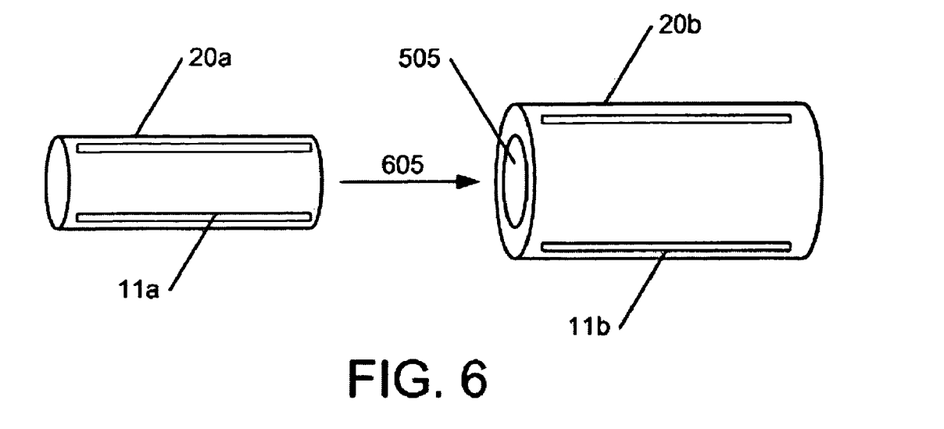
FIG. 6 shows the first and second microstimulators prior to being linked together.

With reference to FIG. 6, the first and second microstimulators 20a and 20b are inductively coupled by sliding the first microstimulator 20a into the cavity 505 of the second microstimulator 20b, as exhibited by the arrow 605 in FIG. 6. As mentioned, the cavity 505 forms an opening in one end of the second microstimulator 20b. The opening is sized to receive the first microstimulator 20a therethrough.

Figure 7A:
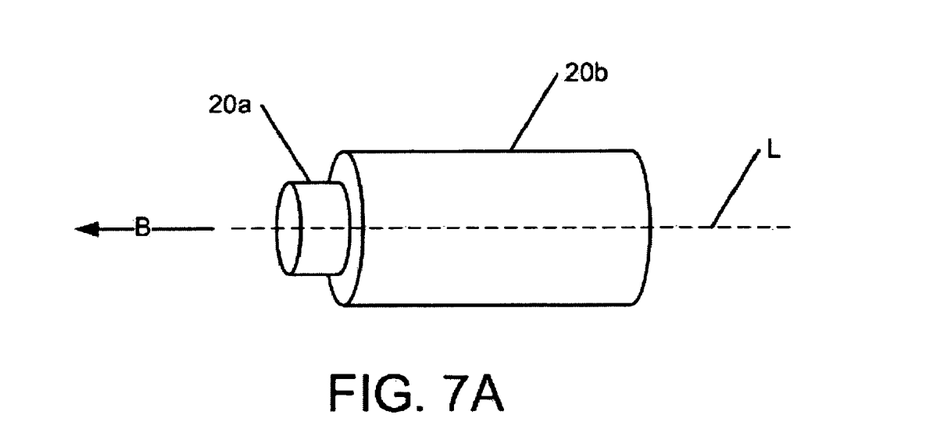
FIG. 7A shows a first embodiment of the microstimulators linked together.
Figure 7B:
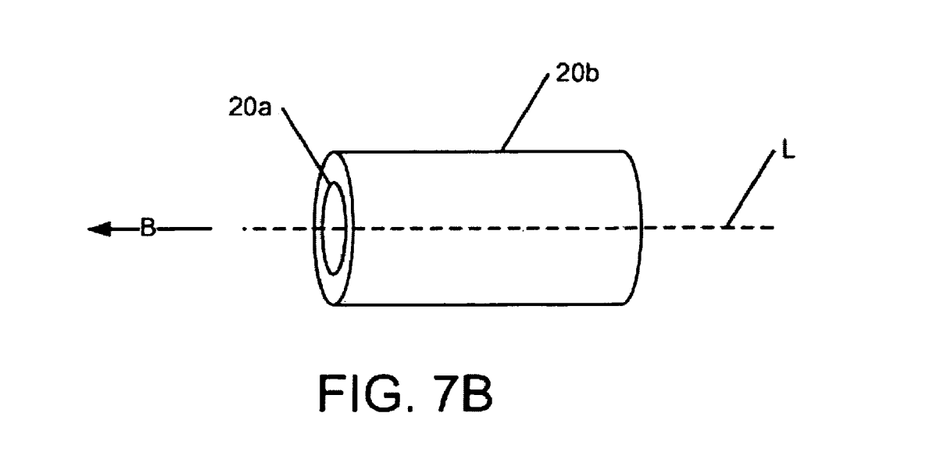
FIG. 7B shows a second embodiment of the microstimulators linked together.

The first microstimulator can be sized to protrude out of the cavity 505 when positioned therein or can be sized such that it is contained entirely within the cavity. With reference to FIG. 7A, when the first microstimulator 20a is fully positioned in the cavity 505, a portion of the first microstimulator 20a can protrude outwardly from the cavity 505. Alternately, the first microstimulator 20a can be entirely positioned within the cavity 505 such that none or substantially none of the first microstimulator 20a protrudes outwardly, as shown in FIG. 7B.

As mentioned, the annular coils 11a and 11b (FIG. 6) of the respective microstimulators are disposed about the longitudinal axes L1 and L2 (FIGS. 5A and 5B) of the microstimulators 20. When the first microstimulator 20a is positioned inside the second microstimulator 20b, the axes L1 and L2 are aligned along a common axis L, as shown in FIGS. 7A and 7B. The inductive coils are thus disposed about the axis L and are energized to generate electromagnetic fields B for inductive coupling of the devices.

It should be appreciated that both magnetic fields B generated by the annular coils will be co-axially aligned with the axis L. The alignment of the magnetic fields forms a generally strong inductive coupling between the coils of the first and second microstimulators 20. Moreover, because the first microstimulator 20a is positioned inside of the second microstimulator 20b and the two are aligned along a common axis L, the two devices collectively use up less space than if placed side by side.

If desired, the first microstimulator 20a can be removed from the second microstimulator 20b after a predetermined time period has elapsed after positioning inside the patient. It is appreciated that some scar tissue may form around the implanted microstimulators. The presence of the scar tissue may interfere with detaching the microstimulators from one another. A scalpel can be used to form a small incision to cut away any scar tissue to release the microstimulators from one another.

The inductive coupling between the microstimulators 20 enables communication between the microstimulators 20, as well as the translation of power between the devices. In this regard, the microstimulators 20 can share the functionality of electronic circuitry, such as, for example, an integrated circuit, that is present on only one of the microstimulators. This enables one of the microstimulators 20 to be relatively compact in that it is not required to include the electronic components that are located on the other microstimulator 20. Furthermore, sharing of electronic components permits the first microstimulator 20a to be configured with the cavity 505 where electronic components might otherwise be located.

Pursuant to a method of use, a clinician is provided with first and second microstimulators 20a and 20b that are configured as shown and described with reference to FIGS. 5A and 5B. The clinician implants the microstimulators within a patient's body and mechanically, electronically, and communicatively couples the microstimulators to one another. The coils of the first and second microstimulators are energized to generate a magnetic field that inductively couples the microstimulators.

The microstimulators 20 may be implanted with a surgical tool such as a tool specifically designed for the purpose, or may be placed, for instance, via a small incision and through an insertion cannula. Alternatively, the microstimulators may be implanted via conventional surgical methods, or may be implanted using other endoscopic or laparoscopic techniques. A more complicated surgical procedure may be required for sufficient access to a portion of a nerve and/or for fixing the microstimulator in place.

The first microstimulator 20a can be inserted into the second microstimulator 20b either before or after the devices are implanted into the patient. The microstimulators 20 can be part of a stimulator system 200 that includes an internal portion 202 and an external portion 204, as described with reference to FIG. 2. After the passage of a period of time, the microstimulators 20a, 20b, or both microstimulators 20 can be removed from the patient.

Figure 8:
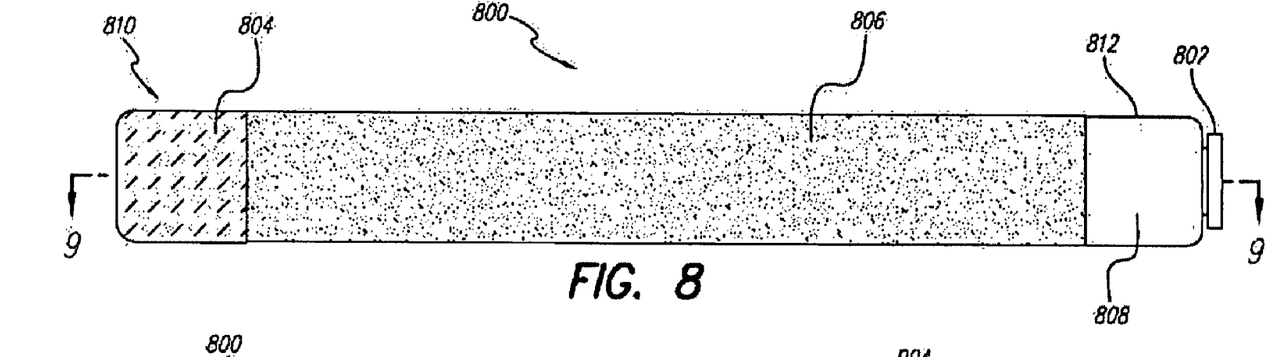
FIG. 8 shows a side view of another embodiment of a microstimulator.
Figure 9:
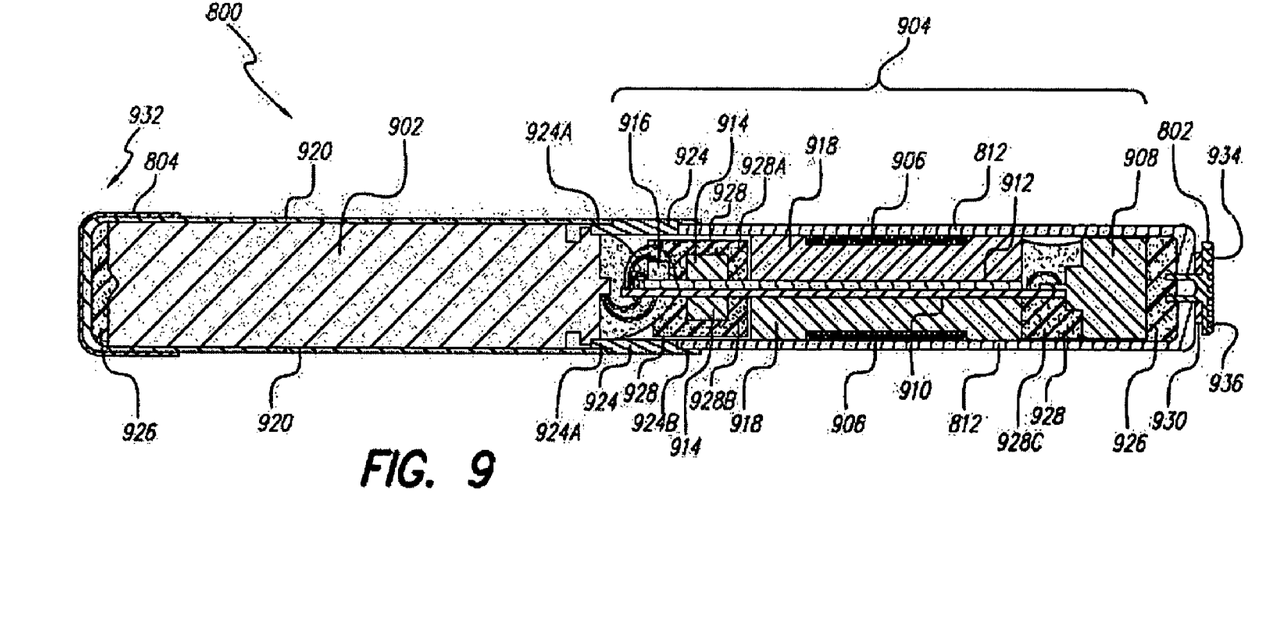
FIG. 9 shows a cross section view of the microstimulator of FIG. 8.
Figure 10:
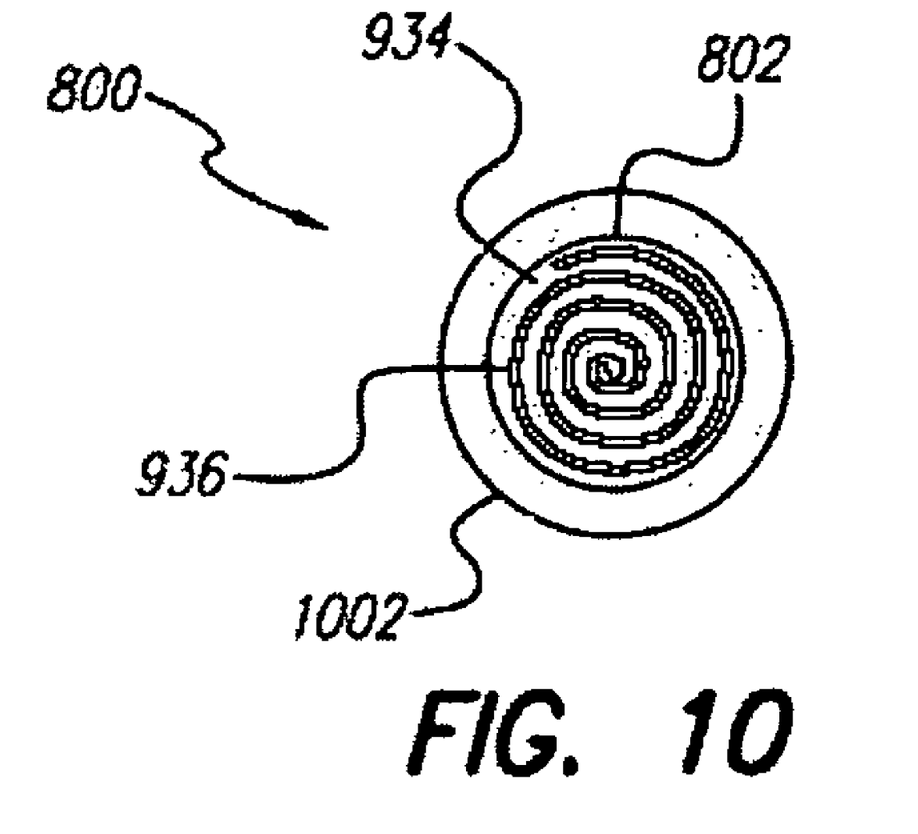
FIG. 10 shows an end view of the microstimulator of FIG. 8.

FIGS. 8, 9, and 10 present another implementation of a microstimulator, referred to as stimulator 800. In particular, FIG. 8 shows a side view of a stimulator 800, FIG. 9 shows a sectional view of the stimulator 800 along the line 9-9 in FIG. 8, and FIG. 10 shows an end view of the stimulator 800.

The stimulator 800 includes a pair of electrodes 802 and 804, a power source 902, an electronic subassembly 904, and a case 1002. The button electrode 802 is an active/stimulating electrode whereas electrode 804 is an indifferent/reference electrode. The pair of electrodes 802 and 804 can be made from any of the materials discussed above.

The power source 902 provides power for the delivery of electrical stimuli to tissue through the pair of electrodes 802 and 804. In an implementation, the power source 902 can be a rechargeable power source, such as a rechargeable battery, a capacitor, or the like. When the power source 902 is a rechargeable battery, it can be a lithium-ion battery or other suitable type of battery that can be recharged through the use of a charging field or other form of power transfer. One type of rechargeable battery that can be used is disclosed in International Publication WO 01/82398 A1, published 1 Nov. 2001, and/or WO 03/005465 A1, published 16 Jan. 2003, the contents of both of which are incorporated herein by reference. Other battery construction techniques that can be used to make the power source 902 include those shown, e.g., in U.S. Pat. Nos. 6,280,873; 6,458,171, and U.S. Publications 2001/0046625 A1 and U.S. 2001/0053476 A1, the contents of all of which are also incorporated herein by reference. Recharging can be performed using an external charger in the manner described above.

The electronic subassembly 904 includes a coil 906 and a stimulating capacitor 908. The button electrode 802 is coupled to the electronic subassembly 904 through the stimulating capacitor 908. The coil 906 can receive power for charging the power source 902 using power received from the charging field.

The electronic subassembly 904 also can comprise circuitry for stimulation, telemetry, production testing, behavioral control, and battery charging, including a non-crystal oscillator. The stimulation circuitry can be further divided into components for high voltage generation, stimulation phase current control, recovery phase current control, charge balance control, and over voltage protection circuitry. The telemetry circuitry can be further divided into an on-off keying (OOK) receiver, a frequency shift keying (FSK) receiver, and an FSK transmitter. The behavioral control circuitry can be further divided into components for stimulation timing, high voltage generation closed loop control, telemetry packet handling, and battery management. In addition to these functions, there is circuitry for reference voltage and reference current generation, system clock generation, and Power-On Reset (POR) generation.

In operation, charging circuitry within the electronic subassembly 904 can detect the presence of an external charging field, such as the charging field. Upon detection, the stimulator 800 can receive a telemetry message and recharge the power source 902, as necessary. As described above, the electronic subassembly 904 can measure a voltage during recharging and transmit the measured voltage value to an external device, such as the external portion 204 of the stimulator system 200 (FIG. 2). Battery voltage measurements can be made at times when stimulation pulses are not being delivered. U.S. Pat. No. 6,553,263, incorporated herein by reference, describes charging technology that also can be used.

As another example, when the power source 902 used within the stimulator 800 is a capacitor used in combination with a primary battery and/or a rechargeable battery, the electronic subassembly 904 can use the charge stored on the capacitor to power the stimulator 800 during times of peak power demand. Such times include times when telemetry signals are being transmitted from the stimulator 800 to one or more external device(s), or when the amplitude of the stimulation pulses has been programmed to be relatively high. When used in combination with a rechargeable battery, the electronic subassembly 904 can use the charge stored on the capacitor to recharge the rechargeable battery or to power the stimulator 800 at times of high power demand.

The electronic subassembly 904 also can include protection circuitry to act as a failsafe against battery over-voltage. A battery protection circuit can continuously monitor a battery's voltage and electrically disconnect the battery if its voltage exceeds a preset value. Further, the electronic subassembly 904 can include a memory and a processor and/or other electronic circuitry that allow it to generate stimulating pulses that are applied to a patient through the pair of electrodes 802 and 804 in accordance with logic located within the electronic subassembly 904. The processor and/or other electronic circuitry also can control data communication with an external device, such as the external portion 204 of the stimulator system 200 (FIG. 2). The processor and/or other electronic circuitry can allow the stimulator 800 to perform processes described above.

The electronic subassembly 904 also can include a panel 910, integrated circuitry 912, capacitors 914, diodes 916, and two ferrite halves 918. The arrangement of these components in electronic subassembly 904 is described in U.S. Patent Publication No. 2005/0021108, the contents of which is incorporated herein by reference.

The stimulator 800 can have a case 1002 characterized by a tubular, cylindrical, or rectangular shape with an outer dimension greater than about 3.20 mm and less than about 3.70 mm. For example, the case 1002 can have an outer diameter of about 3.30 mm. Additionally, the case 1002 can have an inner diameter that encloses the electronic subassembly 904 and is greater than about 2.40 mm and less than about 2.54 mm. The case 1002 also can have an inner diameter that encloses the power source 902 and is greater than about 2.92 mm and less than about 3.05 mm. The length of the case 1002 can be less than about 30.00 mm, and greater than about 27.00 mm. The portion of the case 1002 that encloses the electronic subassembly 904 can be less than about 13.00 mm in length and the portion of the case 1002 that encloses the power source 902 can be about 11.84 mm in length. These dimensions are only examples and can be changed to accommodate different types of power sources. For example, the stimulator 800 can have a rectangular or ovoid cross section instead of being cylindrically shaped. Additionally, the case 1002 can be Magnetic Resonance Imaging (MRI) compatible.

The case 1002 can be sealed to protect the electrical components contained within the stimulator 800. For example, the case 1002 can be hermetically-sealed and made from two cylindrical cases, namely, a titanium 6/4 case 920 and a zirconia ceramic case 812. Other materials and shapes for the case 1002 also can be used. A titanium 6/4 or other suitable connector 924 can be brazed with a titanium nickel alloy (or other suitable material) to ceramic case 812 for securing the mating end of titanium case 920. A connector 924 has an inside flange 924A and an outside flange 924B which serve to "self center" the braze assembly. Before inserting the subassembly and before securing the mating ends, conductive silicone adhesive 926 can be applied to the inside end of the ceramic shell as well as to the inside end of the titanium shell. A molecular sieve moisture getter material 928 is also added to areas 928A, 928B, and 928C (FIG. 9) before the brazing process.

The "spiral" self centering button electrode 802 can be made from titanium 6/4 or other suitable material and plated with an iridium coating or other suitable conductive coating. An end view of the button electrode 802 is shown in FIG. 10. A spiral groove 936 can be made in stimulating surface 934 of the button electrode 802. Other groove shapes, such as a cross hatch pattern or other patterns can also be used to increase the area of the stimulating surface 934 of the button electrode 802.

The sharp edges in groove 936 can force a more homogeneous current distribution over the stimulating surface 934 and decrease the likelihood of electrode corrosion over time by reducing current density along the sharp groove edges. A tool made in the shape of a trapezoid or similar shape can be used to cut the groove 936 into a spiral or other shape. Other devices for cutting the groove 936 can be used such as, e.g., ion beam etching.

The button electrode 802 can act as active or stimulating electrode. A titanium/nickel alloy 930 or other suitable material can be used to braze the button electrode 802 to the zirconia ceramic case 812. An end view of the stimulator 800 is shown in FIG. 10, where the end view of the stimulating "spiral" button electrode 802 can be seen. The end 932 of the titanium shell 920 can be plated with an iridium coating (other suitable conductive coating can be applied), which plated area becomes the indifferent iridium electrode 804.

FIG. 8 shows a top view of the stimulator 800 with the external coatings depicted. A type C parylene or other suitable electrically insulating coating can be applied to the shaded area 806, e.g., by standard masking and vapor deposition processes. The zirconia ceramic case 812 is left exposed in area 808 and the iridium electrode 804 is shown on the end 810 of the titanium case 920.

U.S. Pat. No. 6,582,441, incorporated herein by reference, describes a surgical insertion tool which can be used for implanting the stimulator 800. The procedures taught in the '441 patent for using the tool and associated components can be used for implanting and extracting the stimulator 800. The surgical insertion tool described in the '441 patent facilitates the implantation of the stimulator 800 in a patient so that the button electrode 802 is proximate to a nerve site (e.g., near the pudendal nerve for treating patients with urinary urge incontinence). The distance between the button electrode 802 and the nerve site can be, for example, less than 1-2 mm.

Figure 11:
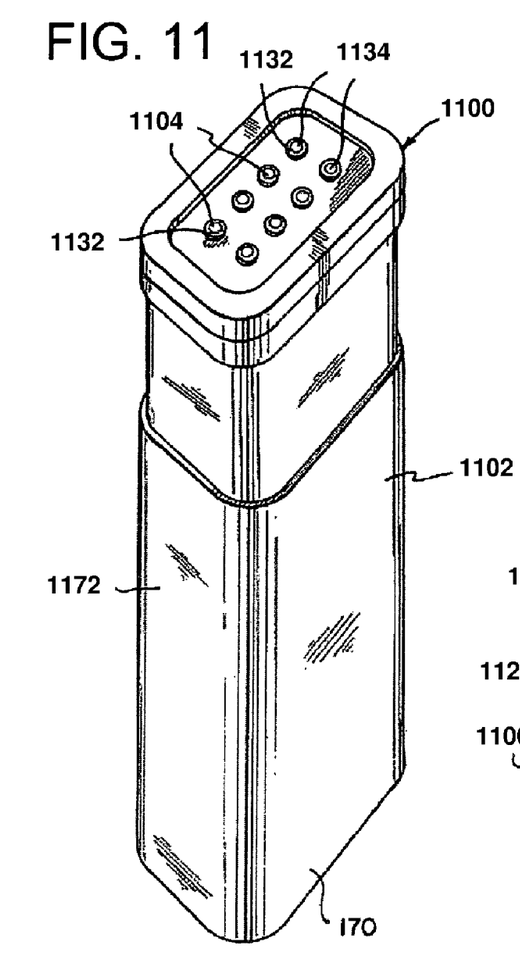
FIG. 11 shows a perspective view of another embodiment of a portion of a microstimulator.

FIG. 11 shows a perspective view of a first portion 1100 of another implementation of a microstimulator. The implantable microstimulator includes a housing 1102, a power source 1120, an electronics subassembly 1122, an optional antenna 1124, one or more conductors 1127 extending from the electronics subassembly 1122 to the conductive via(s) 1104, and one or more conductive vias 1104 extending through the housing to couple the electronic subassembly to electrodes disposed on the exterior of the housing. Other embodiments of an implantable microstimulator may include more or fewer components. It will be understood that the power source 1120, components of the electronics subassembly 1122, and/or the optional antenna 1124 can be provided outside of the housing in a separate unit and coupled to the implantable microstimulator by a lead. Examples of such arrangements are described in U.S. patent application Ser. No. 11/056,762, incorporated herein by reference.

Figures 13, 14:
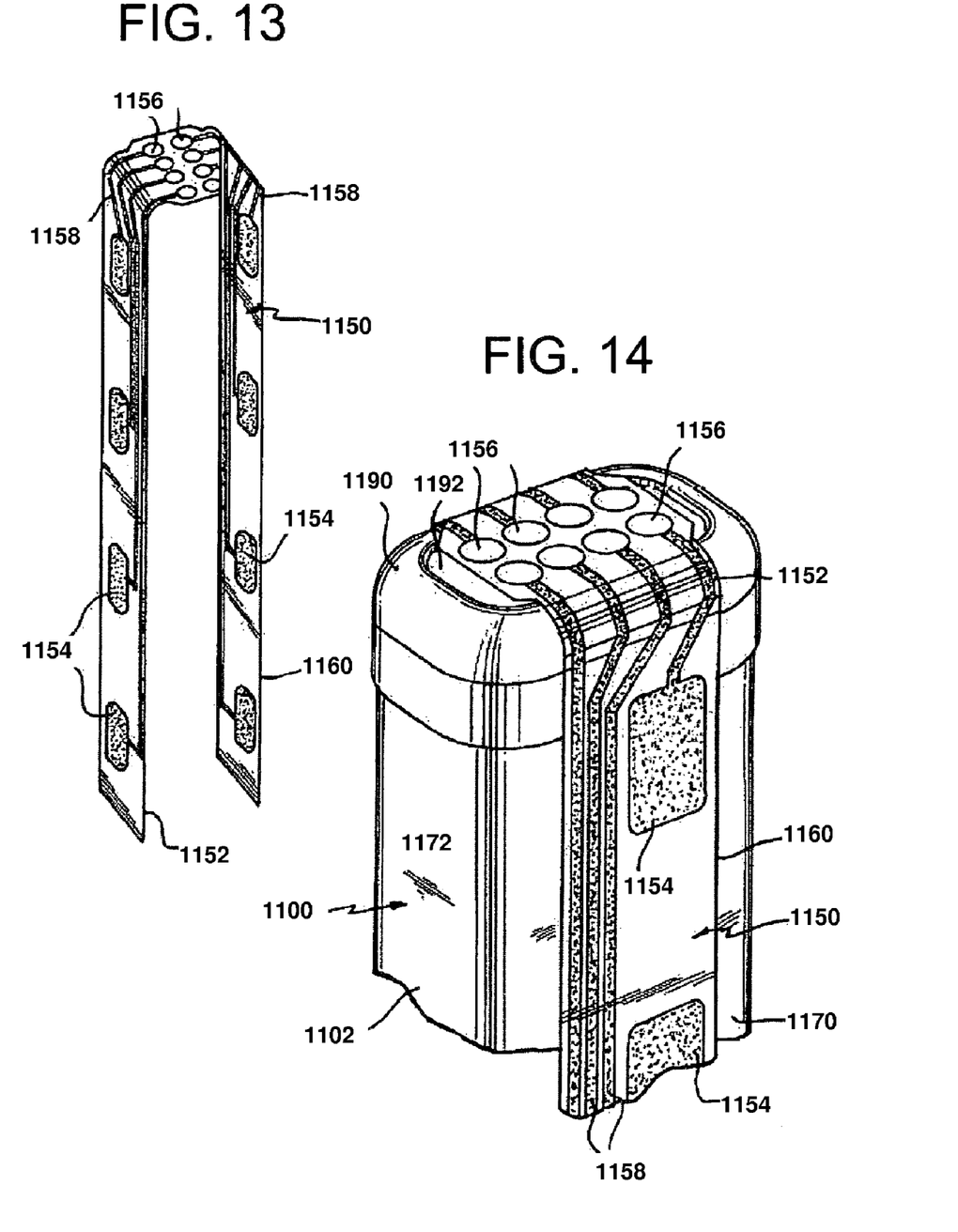
FIG. 13 is a perspective view of one embodiment of external electrodes disposed on a film substrate for use in a microstimulator.
FIG. 14 is a perspective view of the portion of FIG. 12 and the electrodes/substrate of FIG. 13 disposed together to form a microstimulator.

FIG. 13 illustrates a second portion 1150 of the implantable microstimulator. This portion includes a first substrate 1152, one or more electrodes 1154, one or more contact pads 1156, conductor(s) 1158 coupling the electrode(s) 1154 to the contact pad(s) 1156, and optionally a second substrate 1160 disposed over the first substrate so that at least a portion of the conductors is disposed between the first and second substrates. Optionally, a second substrate 1160 is disposed over at least a portion of the contact pads 1156 and/or conductors 1158. The second substrate can be a single piece of material or can be several separate pieces. The second substrate 1160 can optionally leave at least a portion of the electrodes 1154 exposed.

Figure 12:
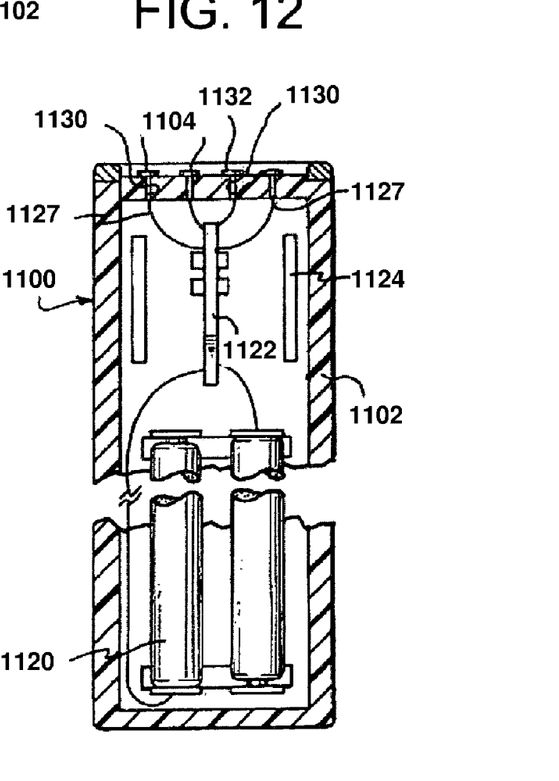
FIG. 12 is a cross-sectional view of one embodiment of a portion of the microstimulator of FIG. 11.

FIG. 14 illustrates the two portions 1100, 1150 coupled together with the contact pads 1156 disposed over the vias 1104 (FIG. 11) so that the electrode(s) 1154 are coupled to the electronic subassembly 1122 (FIG. 12) within the housing 1102. Each via 1104 includes a channel 1130 (FIG. 12) through the housing, a capture pad 1132 disposed on the surface of the housing 1102, and an optional protrusion 134 (FIG. 11) that can facilitate alignment and contact with the contact pads 1156.

The housing 1102 can have any shape including, for example, cylindrical, parallelepiped, cubic, and the like. In at least some embodiments, a non-cylindrical shape (for example, a parallelepiped shape) is preferred. The non-cylindrical shape can aid a practitioner in positioning the microstimulator correctly in relation to the tissue to be stimulated. In some embodiments, the shape has sides which are distinguishable based on at least one dimension. In the illustrated embodiment of FIGS. 11-14, the housing 1102 has a roughly parallelepiped shape with two opposing sides 1170 that are wider than two adjacent sides 1172.

The optional antenna 1124 can have any form. In one embodiment, the antenna 1124 comprises a coiled wire that is wrapped at least partially around the electronic subassembly within or on the housing. In this regard, the microstimulator of FIGS. 11-14 can be configured to be inserted into a complementary-shaped cavity of a second microstimulator, such as in the manner described above with reference to FIGS. 5-7. A magnetic field generated by the antenna 1124 can be co-axially aligned with a magnetic field generated by an antenna device in the second microstimulator.

Figure 15:
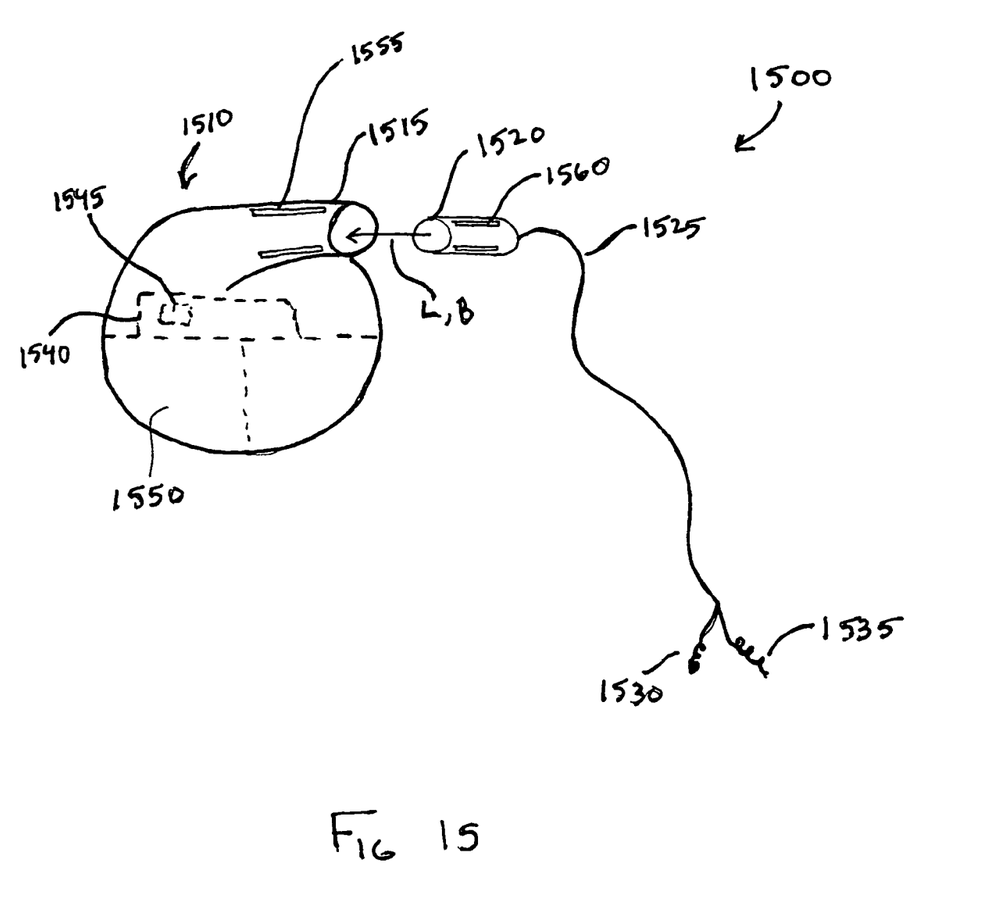
FIG. 15 shows an implantable pulse generator that removably couples to a lead with electrodes for stimulating a nerve.

FIG. 15 shows an implantable pulse generator (IPG) system 1500 that utilizes inductive coupling of a pair of coils in the manner described above. The IPG system 1500 includes an IPG 1510 having a socket 1515 that defines a cavity sized to receive a lead coupler 1520. A lead 1525 extends outwardly from the coupler 1520 and includes a pair of electrodes 1530, 1535 that can be positioned at or near nerves for stimulation. The IPG 1510 includes circuitry 1540 containing a microprocessor 1545 that is driven by one or more batteries 1550, such as, for example, Lithium Thionyl Chloride batteries.

The socket 1515 includes an annular coil 1555 that is generally annularly positioned around a longitudinal axis L of the socket 1515. Likewise, the coupler 1520 includes an annular coil 1560 that is generally annularly positioned around a longitudinal axis that can be co-axially aligned with the axis L1 of the socket 1515.

The cavity of the socket 1515 has a size and shape that conforms to the size and shape of the coupler 1520. That is, the socket cavity is sized and shaped to receive the coupler 1520 therein, such as in a sliding fashion. Although the coupler 1520 is shown in FIG. 15 having a cylindrical shape, it should be appreciated that the coupler 1520 can have other shapes, such as rectangle, square, oval, etc.

The annular coils 1555 and 1560 of the socket 1515 and the coupler 1520 are disposed about a common axis L when the coupler 1520 is positioned in the cavity of the socket 1515. The inductive coils are thus disposed about the axis L and are energized to generate electromagnetic fields B for inductive coupling of the coupler 1520 to the IPG 1510 via the socket 1515.

It should be appreciated that both magnetic fields B generated by the annular coils 1555, 1560 are co-axially aligned with the axis L when the coupler 1520 is positioned inside the socket 1515. The alignment of the magnetic fields forms a generally strong inductive coupling between the coils of the socket 1515 and the coupler 1520. Thus, the socket-coupler arrangement permits strong inductive coupling between the IPG 1510 and the lead 1525. In addition, the arrangement provides for removable coupling between the IPG 1510 and the lead 1525. This permits the IPG to be removed from the patient by uncoupling the coupler 1520 from the socket 1515. Because the socket 1515 detaches from the lead coupler 1520, the IPG 1510 can be removed (such as for replacement, upgrade, maintenance, etc.) without disturbing the accurate placement of the electrodes 1530, 1535 relative to the nerves.

A number of implementations have been disclosed herein. Nevertheless, it will be understood that various modifications may be made without departing from the spirit and scope of the claims. Accordingly, other implementations are within the scope of the following claims.

What is claimed is:

1. A system comprising:
a first stimulator configured to be wholly implanted in a body of a patient, the first stimulator having a first coil;
a second stimulator configured to be wholly implanted in a body of a patient, the second stimulator having a second coil;
wherein the first stimulator forms a cavity with at least one opening within which the second stimulator is positionable to arrange the first and second coils such that, in operation, magnetic fields generated by the first and second coils are aligned along a common axis.

2. The system of claim 1, wherein the first stimulator is cylindrical.

3. The system of claim 1, wherein the cavity is cylindrical.

4. The system of claim 1, wherein the first and second stimulators each comprise a pair of electrodes arranged and configured to deliver electrical stimulation to surrounding tissue.

5. The system of claim 4, wherein the pair of electrodes comprises a stimulating electrode configured to stimulate the tissue and an indifferent electrode.

6. The system of claim 1, wherein the first and second stimulators magnetically couple to one another.

7. The system of claim 1, wherein each of the first and second stimulators are one of an implantable pulse generator, a spinal cord stimulator, a cochlear implant, a deep brain stimulator, a drug pump, a microstimulator, or a micro-drug pump.

8. The system of claim 1, wherein the first and second coils both comprise annular coils that are disposed along a common axis.

9. The system of claim 1, wherein the first coil is positioned around the cavity.

10. The system of claim 1, wherein the first stimulator has first control circuitry configured for controlling stimulation energy output by the first stimulator, and a first housing hermetically containing the first control circuitry, and the second stimulator has second control circuitry different from the first control circuitry and configured for controlling stimulation energy output by the second stimulator, and a second housing hermetically containing the second control circuitry.

11. The system of claim 10, wherein the first stimulator has a first power source hermetically contained within the first housing, and the second stimulator has a second power source hermetically contained within the second housing.

12. The system of claim 10, wherein the first stimulator has a first programmable memory hermetically contained within the first housing, and the second stimulator has a second programmable memory hermetically contained within the second housing.

13. The system of claim 1, further comprising an external controller configured to inductively communicate with the first and second stimulators via the respective first and second coils.

14. A stimulator for wholly implanting in a patient, comprising: a housing having a cavity sized to receive a second stimulator, wherein the cavity is exposed to the exterior of the housing; and
a first coil configured to generate a magnetic field,
wherein the second stimulator is configured to be wholly implanted within the patient and the first coil and the cavity are arranged so that the magnetic field is to be aligned along a common axis with a magnetic field generated by a second coil of the second stimulator with the second stimulator positioned in the cavity.

15. The stimulator of claim 14, further comprising a pair of electrodes configured to deliver electrical stimulation to surrounding tissue.

16. The stimulator of claim 15, wherein the first coil is configured to magnetically couple to the second coil with the second stimulator positioned in the cavity.

17. The stimulator of claim 15, wherein the first coil comprises an annular coil disposed about the common axis.

18. The stimulator of claim 14, wherein the first coil is positioned around the cavity.

19. A method, comprising:
inserting a first stimulator into a cavity in a second stimulator, wherein the cavity has at least one opening;
wholly implanting the first stimulator and the second stimulator in a body of a patient, the first stimulator including a first coil and the second stimulator including a second coil; and
generating, with the first and second coils, magnetic fields aligned along a common axis.

20. The method of claim 19, wherein the first stimulator is inserted into the cavity prior to the implanting of the first and second stimulators into the body of the patient.

21. The method of claim 19, further comprising removing the first stimulator from the second stimulator without disturbing a positioning inside the patient of electrodes connected to the first stimulator.

22. A system of magnetically coupled stimulators, comprising:
a first stimulator configured to be wholly implanted in a body of a patient comprising a first coil and a first electrical connection to a first collection of one or more electrodes configured to deliver electrical stimulation to surrounding tissues and nerves; and
a second stimulator configured to be wholly implanted in a body of a patient comprising a second coil, a second electrical connection to a second collection of one or more electrodes configured to deliver electrical stimulation to surrounding tissues and nerves, and a cavity forming at least one opening that is sized and shaped to receive at least a portion of the first stimulator,
wherein the cavity and the first and second coils are positioned so that the first and second coils are co-axially aligned when the portion of the first stimulator is received in the cavity.

23. The system of claim 22, wherein the first stimulator is sized to protrude out of the cavity.

24. The system of claim 22, wherein the first stimulator is sized to be contained with the cavity.

25. The system of claim 22, wherein the second coil is positioned around the cavity.

* * * * *